(12) United States Patent
Triplett, II et al.

(10) Patent No.: US 6,583,320 B2
(45) Date of Patent: *Jun. 24, 2003

(54) PROCESS FOR PREPARING 4-AMINODIPHENYLAMINE INTERMEDIATES

(75) Inventors: Ralph Dale Triplett, II, Wadsworth, OH (US); Roger Keranen Rains, Richfield, OH (US)

(73) Assignee: Flexsys America L.P., Akron, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/143,478

(22) Filed: May 10, 2002

(65) Prior Publication Data

US 2003/0088127 A1 May 8, 2003

Related U.S. Application Data

(63) Continuation-in-part of application No. 09/911,058, filed on Jul. 23, 2001, now Pat. No. 6,395,933.

(51) Int. Cl.$^7$ .............................................. C07C 209/36
(52) U.S. Cl. ..................... 564/420; 564/421; 564/422; 564/423; 564/398; 564/397; 564/408; 564/433; 564/434
(58) Field of Search ................................. 564/420, 421, 564/422, 423, 398, 397, 408, 433, 434

(56) References Cited

U.S. PATENT DOCUMENTS 6,395,933 B1 * 5/2002 Triplett, II et al.

OTHER PUBLICATIONS

Goldberg, Y. et al, *Tetrahedron, Elsevier Science Publishers, Amsterdam, NL, Betaines derived from amino and hydrazino acids as phase transfer catalysts*, vol. 46, No., 1990, pp. 111922, XP002113890, ISSN: 040402, abstact, p. 1912.
Stern, M.K. et al.: *J. Am. Chem. Soc., Direct coupling of aniline and nitrobenzene: A new example of nucleophilic aromatic substitution for hydrogen*, vol. 114, No. 23, 1992, pp. 9237–9238, XP002216864).

* cited by examiner

Primary Examiner—Samuel Barts
(74) Attorney, Agent, or Firm—Louis A. Morris

(57) ABSTRACT

The invention is directed-to a method of producing one or more 4-aminodiphenylamine intermediates comprising the steps of bringing an aniline or aniline derivative and nitrobenzene into reactive contact and reacting the aniline and nitrobenzene in a confined zone at a suitable time and temperature, in the presence of a mixture comprising an inorganic salt or metal organic salt having a cation that would be a suitable cation of a strong inorganic base, an oxidant and an organic base, the mixture not including a reaction product of betaine and a strong inorganic base.

27 Claims, No Drawings

PROCESS FOR PREPARING 4-AMINODIPHENYLAMINE INTERMEDIATES

CROSS REFERENCE TO RELATED APPLICATION

This application is a continuation-in-part of U.S. patent application Ser. No. 09/911,058, filed Jul. 23, 2001, now U.S. Pat. No. 6,395,433 the contents of which is incorporated herein in its entirety.

BACKGROUND OF THE INVENTION

1. Field of the Invention

The present invention relates to a process for preparing 4-aminodiphenyl-amines intermediates.

2. Related Art

4-Aminodiphenylamines are widely used as intermediates in the manufacture of alkylated derivatives having utility as antiozonants and antioxidants, as stabilizers for monomers and polymers, and in various specialty applications. For example, reductive alkylation of 4-aminodiphenylamine (4-ADPA) with methylisobutyl ketone provides N-(1,3-dimethylbutyl)-N'-phenyl-p-phenylene-diamine, which is a useful antiozonant for the protection of various rubber products.

4-Aminodiphenylamine derivatives can be prepared in various ways. An attractive synthesis is the reaction of an optionally substituted aniline with an optionally substituted nitrobenzene in the presence of a base, as disclosed, for example, in U.S. Pat. No. 5,608,111 (to Stern et al.) and U.S. Pat. No. 5,739,403 (to Reinartz et al.).

U.S. Pat. No. 5,608,111 describes a process for the preparation of an optionally substituted 4-ADPA wherein in a first step optionally substituted aniline and optionally substituted nitrobenzene are reacted (coupled) in the presence of a base. In working examples, aniline and nitrobenzene are reacted in the presence of tetramethylammonium hydroxide as the base, and water and aniline are azeotropically removed during the coupling reaction.

International publication WO 00/35853 discloses a method of preparation of intermediates of 4-aminodiphenylamine by the reaction of aniline with nitrobenzene in a liquid medium where the reaction system consists of a solution of salts of true zwitterions with hydroxides. A combination of potassium hydroxide and betaine hydrate is exemplified. The reaction may take place in the presence of free oxygen.

EP publication 566 783 describes a method of manufacture of 4-nitrodiphenylamine by the reaction of nitrobenzene with aniline in the medium of a polar aprotic solvent in a strongly alkaline reaction system. A phase transfer catalyst such as tetrabutylammonium hydrogen sulfate is employed. This reference requires that the reaction be carried out in an oxygen-free atmosphere in order to prevent undesirable side reactions caused by oxidation.

U.S. Pat. No. 5,117,063 and International publication WO 01/14312 disclose processes for preparing 4-nitrodiphenylamine and 4-nitrosodiphenlamine, using an inorganic base with crown ether, a phase transfer catalyst.

U.S. Pat. No. 5,453,541 teaches that an external desiccant, such as anhydrous sodium sulfate, may be used to absorb excess water in an anaerobic process for producing one or more 4-ADPA intermediates in which substituted aniline derivatives and nitrobenzene are brought into reactive contact.

The objective of the present invention is to provide a superior method for producing one or more 4-ADPA intermediates by reacting aniline and nitrobenzene in the presence of an organic base and an inorganic salt or a metal organic salt.

SUMMARY OF THE INVENTION

In brief summary, the primary embodiment of the present invention is for a method of producing one or more 4-aminodiphenylamine intermediates comprising the steps of:

(a) bringing an aniline or aniline derivative and nitrobenzene into reactive contact; and (b) reacting the aniline and nitrobenzene in a confined zone at a suitable time and temperature, in the presence of a mixture comprising an inorganic salt or metal organic salt, or mixtures thereof, having a cation that would be a suitable cation of a strong inorganic base, an oxidant and one or more of an organic base selected from the group of compounds defined by:

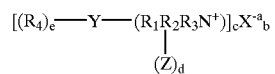

$$[(R_4)_e\text{—}Y\text{—}(R_1R_2R_3N^+)]_c X^{-a}_b \quad \text{I}$$
$$|$$
$$(Z)_d$$

where $R_1$, $R_2$, $R_3$ are the same or different and selected from any straight chain or branched alkyl group containing from 1 to about 20 carbon atoms, e is a whole number integer of value 0, 1, 2 or 3, $(R_4)_e$ is hydrogen for e=0, $R_4$ is $R_1R_2R_3N^+$ for e=1, 2, or 3, X is an anion capable of abstracting a proton from the nitrogen of an aniline or aniline derivative, Y is alkyl, aryl, alkyl aryl or benzyl and substituted derivatives thereof, Z is a substituent selected from the group consisting of hydroxyl, halo, and other hetero atoms, where a=the valence of the anionic moiety and is a whole number integer of 1, 2, 3 or 4, b and c are whole number integers of value 1, 2, 3 or 4 and d is a whole number integer of value 0, 1, 2, 3 or 4, said mixture not including a reaction product of betaine and a strong inorganic base.

Other embodiments of the present invention encompass details about reaction mixtures and ratios of ingredients and particular inorganic salts or metal organic salts and organic bases, all of which are hereinafter disclosed in the following discussion of each of the facets of the present invention.

DETAILED DESCRIPTION OF THE INVENTION

The present invention is directed to a method, as described above, for making intermediates of 4-ADPA that has superior yield and selectivity for those intermediates. Such intermediates comprise 4-nitroso- and/or 4-nitrodiphenylamines (p-NDPA and 4-NDPA, respectively) and salts thereof. The intermediates may then be hydrogenated to produce 4-aminodiphenylamine.

An example of a substituted and multifunctional organic base that is consistent with the above formula I is (2S, 3S)-bis(trimethylammonio)-1,4-butanediol dihydroxide. Other effective organic bases fitting formula I, in addition to those shown in the following examples, can be derived from tetraalkylammonium phase transfer catalysts, wherein the anion is replaced by hydroxide or other suitable anion form, in the literature such as C. M. Starks and C. Liotta, Phase Transfer Catalysis, Principles and Techniques, Academic Press, 1978 and W. E. Keller, Fluka compendium, Vol. 1,2,3, Georg Thieme Verlag, New York, 1986, 1987, 1992.

In previous work a phase transfer catalyst was employed with a strong inorganic base, however the method of the present invention achieves equivalent results by starting with an organic base and an inorganic salt or a metal organic salt. The organic base is defined by the formula above. The examples in the previous work that illustrate the effect of variables should pertain in general to the present invention with the appropriate substitutions of organic base plus inorganic salt for the phase transfer catalyst plus inorganic base.

Organic bases known or believed to be particularly effective in the method of the invention include quaternaryammonium hydroxides selected from the group consisting of, but not limited to, tetramethylammonium hydroxide, tetrabutylammonium hydroxide, methyltributylammonium hydroxide, benzyltrimethylammonium hydroxide (Triton B), tricaprylmethylammonium hydroxide, cetyltrimethylammonium hydroxide and choline hydroxide, and equivalent quaternaryammonium alkoxides, acetates, carbonates, bicarbonates, cyanides, phenolics, phosphates, hydrogen phosphates, hypochlorites, borates, hydrogen borates, dihydrogen borates, sulfides, silicates, hydrogen silicates, dihydrogen silicates and trihydrogen silicates.

The term "strong inorganic base" as used with respect to the meaning of a cation of an inorganic salt or metal organic salt is intended to mean a base that is capable of abstracting a proton from the nitrogen of an aniline or aniline derivative, and may include any base having a $pK_b$ less than that about 9.4, which is the $pK_b$ of aniline. Various aniline derivatives may have different $pK_b$ values, but a $pK_b$ of about 9:4 is employed as a general guide. The base will preferably have a $pK_b$ less than about 7.4.

The term "capable of abstracting a proton from the nitrogen of an aniline or aniline derivative" as applied to anion "X" of formula I, is intended to mean an anion also having a $pK_b$ value as discussed above with respect to the strong inorganic base.

Possible anions for "X" in formula I, in addition to hydroxide, include: alkoxide ($pK_b<1$), acetate ($pK_b=9.25$), carbonate ($pK_b=3.75$), bicarbonate ($pK_b=7.6$), cyanide ($pK_b=4.7$), phenolic ($pK_b=4.1$), phosphate ($pK_b=1.3$), hydrogen phosphate ($pK_b=6.8$) and hypochlorite ($pK_b=6.5$), borate ($pK_b<1$), hydrogen borate ($pK_b<1$), dihydrogen borate ($pK_b=4.7$), sulfide ($pK_b=1.1$), silicate ($pK_b=2$), hydrogen silicate ($pK_b=2$), dihydrogen silicate ($pK_b=2.2$) and trihydrogen silicate ($pK_b=4.1$).

While aniline most effectively couples with nitrobenzene, certain aniline derivatives comprising amides such as formanilide, phenylurea and carbanilide as well as the thiocarbanilide can be substituted to produce 4-ADPA intermediates.

Although the reactants of the method of the invention are referred to as "aniline" and "nitrobenzene", and when it is 4-ADPA that is being manufactured the reactants are in fact aniline and nitrobenzene, it is understood that the reactants may also comprise substituted aniline and substituted nitrobenzene. Typical examples of substituted anilines that may be used in accordance with the process of the present invention, in addition to the above amides, include but are not limited to 2-methoxyaniline, 4-methoxyaniline, 4-chloroaniline, p-toluidine, 4-nitroaniline, 3-bromoaniline, 3-bromo-4-aminotoluene, p-aminobenzoic acid, 2,4-diaminotoluene, 2,5-dichloroaniline, 1,4-phenylene diamine, 4,4'-methylene dianiline, 1,3,5-triaminobenzene, and mixtures thereof. Typical examples of substituted nitrobenzenes that may be used in accordance with the process of the present invention include but are not limited to o- and m-methylnitrobenzene, o- and m-ethylnitrobenzene, o- and m-methoxynitrobenzene, and mixtures thereof.

The method of the invention will hereinafter be described with reference to the manufacture of 4-ADPA itself, starting from aniline and nitrobenzene.

The molar ratio of aniline to nitrobenzene in the process according to the present invention is not particularly important, as the process will be effective with an excess of either.

Inorganic salts and metal organic salts that may be used in conjunction with the organic base have a cation that would be a suitable cation of a strong inorganic base. These inorganic salts and metal organic salts are selected from the group consisting of, but not limited to, the fluoride, chloride, bromide, sulfate, hydrogen sulfate, nitrate, phosphate, dihydrogen phosphate, formate, acetate, oxalate, malonate, citrate, tartrate, maleate, chlorate, perchlorate, chromate, rhenate and carbonate salts of cesium, rubidium, potassium and sodium. In the method of the invention, the inorganic salt or metal organic salt may be used in molar ratio to nitrobenzene from about 0.05:1 to about 6.5:1.

Inorganic salts and metal organic salts known or believed to be particularly effective in the process of the present invention are those that afford acceptable solubility for the inorganic salt or metal organic salt-organic base combination in the reaction medium, including the fluoride, chloride, bromide, sulfate, hydrogen sulfate, nitrate, phosphate, formate, acetate and carbonate salts of cesium, rubidium, potassium and sodium and mixtures thereof. It is preferred that mole ratio of organic base used with an inorganic salt or metal organic salt to nitrobenzene is greater than or equal to about 1:1. It is also preferred that mole ratio of inorganic salt or metal organic salt to organic base is greater than or equal to about 1:1. A particularly preferred mole ratio of organic base to nitrobenzene is about 1.1:1 to about 6:1.

It may be desirable to use a combination of an inorganic salt with a metal organic salt, two or more inorganic salts and/or two or more metal organic salts in case one of the salts that is otherwise effective for use in the process of the invention has a corrosive effect on the equipment used with the process. The combination might also provide better results than could be obtained with one salt.

The use of inorganic salts and metal organic salts with the organic base is also believed to reduce undesirable base decomposition.

In the process according to the invention, it should be noted that an organic base with an inorganic salt or a metal organic salt will give some in situ formation of the equivalent inorganic base and a phase transfer catalyst, wherein the anion in formula 1 is the anion from the salt. For example, tetramethylammonium hydroxide plus potassium bromide will give some KOH plus tetramethylammonium bromide. So the invention would include the direct use of an inorganic base with any phase transfer catalyst that can be formed in situ, such as tetramethylammonium bromide, in lieu of tetramethylammonium hydroxide and a bromide salt as separate ingredients.

A particularly preferred combination of organic base and inorganic salt is tetraalkylammonium hydroxide and a salt in which the anion is a halide, such as potassium halide. The reaction would be carried out in aqueous solution with a continuous distillation of aniline-water azeotrope. A preferred halide anion is chloride.

The reactive contact of the process of the invention is carried out in the presence of an oxidant. The oxidant may be free oxygen, or an oxidizing agent such as hydrogen peroxide. Nitrobenzene in excess of that required for the reaction may also function as an oxidizing agent.

The oxidant may need to be present only for part of the time during which the aniline and nitrobenzene react. Partial oxidative conditions are particularly effective for improving selectivity. One of these instances is when an inorganic salt with a fluoride anion is employed in the reaction mixture under partial oxidative conditions. It is believed that better results, conversion and selectivity, would also be obtained under partial oxidative conditions when the salt anion is sulfate, carbonate, or nitrate and other anions that give relatively low selectivity.

The reactive contact may be carried out at a temperature of from about 20° C. to about 150° C. Other conditions for the reactive contact include pressures in the range of from about 20 mbar to about 20 barg. Reaction time is typically less than about 3.5 hours. It is advantageous to agitate the reaction mixture during the entire reaction.

The reaction of step (b) of the present method may be carried out in the presence of not greater than about 10:1 moles water to moles nitrobenzene. The amount of water does not include the water that hydrates with the reactants and/or with compounds formed in the process. When the mixture comprising an organic base and inorganic salt is in aqueous solution, the reaction may be carried out with a continuous distillation of aniline-water azeotrope.

The aqueous phase may be reused to form a new reaction mixture. Fresh organic base and inorganic salt or metal organic salt are added to replace losses by decomposition, by-product formation and solubility in the separated organic phase. Excess Aniline recovered by distillation from the reaction product mixture may be combined with make-up fresh aniline for recycle to form a new reaction mixture. Recovery of excess nitrobenzene is preferably carried out prior to hydrogenation of the 4-ADPA intermediate by a separation step and the recovered nitrobenzene may be combined with make-up fresh nitrobenzene for use in the process, or hydrogenated to aniline.

The method of the present invention for the preparation of 4-aminodiphenylamines intermediates may be conducted as a batch process or may be performed continuously using means and equipment well known to the skilled person.

The reactive contact in step (a) of the method of the invention may occur in a suitable solvent system. A suitable solvent system comprises a polar aprotic solvent. The polar aprotic solvent may be selected form the group consisting of, but not limited to, dimethyl sulfoxide, benzyl ether, 1-Methyl-2-pyrrolidinone and N,N-dimethylformamide.

The invention is illustrated by the following examples.

Experimental conditions are detailed. A flow of air was supplied to the reactor headspace during all or part of charging reactants, heat-up to reaction temperature, nitrobenzene feed and hold, resulting in free oxygen being present during the reaction. Water was removed from the reaction mixture by azeotropic distillation with aniline. However, the reaction can also be effective without the azeotropic removal of water with aniline.

ANALYTICAL

Yields of individual components were determined by external standard HPLC. Approximately 0.6 grams of material to be analyzed is accurately weighed into a 50-mL volumetric flask and diluted with a buffer solution containing 39% v/v water, 36% v/v acetonitrile, 24% v/v methanol and 1% v/v pH 7 buffer. The solution is injected through a 10 μL loop onto a reversed phase Zorbax ODS HPLC column (250×4.6 mm) using a binary gradient pumping system and the following elution gradient at a constant flow rate of 1.5 mL/minute:

| Time, minutes | % A | % B |
|---|---|---|
| 0 | 100 | 0 |
| 25 | 25 | 75 |
| 35 | 0 | 100 |
| 37.5 | 0 | 100 |
| 38 | 100 | 0 |
| 40 | 100 | 0 |

Eluent A is 75% v/v water, 15% v/v acetonitrile and 10% v/v methanol. Eluent B is 60% v/v acetonitrile and 40% v/v methanol. Detection is UV at 254 nm.

Conversion is calculated based on the amount of unreacted nitrobenzene remaining in the final coupling reaction mass. Conversion is assumed to be 100% if no nitrobenzene is detected.

Selectivity is defined by the formula: (p-NDPA Yield+4-NDPA Yield)/(total yield). 4-NDPA is 4-nitrodiphenylamine and p-NDPA is 4-nitrosodiphenylamine. Total yield is the sum of the yield of all known and unknown peaks (assigned an arbitrary mole weight value of 216, aniline+nitrobenzene).

In the table: "An Recr" refers to compounds from which aniline may be easily recovered and is a sum total of trans-azobenzene and azoxybenzene; "Others" are aniline and nitrobenzene coupling by-products e.g. phenazine, N-oxy-phenazine, 2-NDPA, 4-phenazo-diphenylamine and any unknowns.

EXPERIMENTAL

Experimental conditions are detailed within the example.

Example 1

This example demonstrates the reaction of aniline and nitrobenzene in the presence of an oxidant in combination with an aqueous solution of tetramethylammonium hydroxide and various inorganic salts by continuous distillation of the aniline-water azeotrope. The TMAH/salt combination represents an ionic mixture of a potential base recycle stream from a process comprising an inorganic base and phase transfer catalyst after reduction of the coupling reaction mass to 4-ADPA.

Charged to a 500-mL round bottom flask equipped with a Teflon paddle stirrer, thermocouple, nitrobenzene feed tube and air bleed valve were: 139.7 grams aniline (99%, 1.49 moles), 73.9 grams aqueous tetramethylammonium hydroxide solution (35.5%, 0.29 moles) and an equivalent amount of salt (vs. base, in 15% molar excess over nitrobenzene) as listed in Table 1 below. The mixture was heated for 30 minutes at 120 mm Hg and then nitrobenzene feed (30.8 grams, 99%, 0.25 moles) was started. The system pressure was regulated by adjusting the air bleed valve throughout the duration of the reaction cycle to maintain the desired temperature of 80° C. and to complete the NB charge in approximately 75 minutes at a final pressure of 72 mm Hg. The mixture was held for 30 minutes at 70 mm Hg to insure completeness of reaction and then quenched with 25 mL water. Air was bled into the reactor headspace during the entire cycle of charging reactants, heating to reaction temperature, feeding nitrobenzene and holding for reaction completion. The salts are charged in molar equivalence to nitrobenzene at Salt/NB=1.15. For example, potassium carbonate and sodium sulfate have two equivalents of inorganic cation, so that the molar ratio is 0.575.

compounds such as N-Methylaniline and a stench of trimethylamine, both of which are indicative of base degradation.

Example 2

This example demonstrates the effect of the mole ratio of inorganic salt to nitrobenzene. Reaction conditions were comparable to those for Example 1, except that the mole ratio of KCl to nitrobenzene was varied. The results in Table 2 indicate the addition of only a small amount of inorganic salt will increase selectivity. Therefore, in situations where corrosion due to high salt level is a concern, at least a modest selectivity improvement can be obtained.

TABLE 1

|  | Conversion % | Selectivity % | Yield, % | | | |
|---|---|---|---|---|---|---|
|  |  |  | p-NDPA | 4-NDPA | An Recr | Other |
| Comparison: KOH + TMACl,* | 100.0 | 97.9 | 72.6 | 25.3 | 1.9 | 0.2 |
| TMAH Only, No Salt Added | 100.0 | 83.8 | 62.4 | 21.4 | 4.4 | 11.8 |
| 21.44 g Potassium Chloride | 100.0 | 97.2 | 72.3 | 24.8 | 1.5 | 1.4 |
| 16.82 g Sodium Chloride | 62.7 | 97.2 | 15.6 | 45.3 | 0.6 | 1.1 |
| 19.87 g Potassium Carbonate | 100.0 | 89.1 | 72.8 | 16.3 | 3.8 | 7.1 |
| 20.42 g Sodium Sulfate | 100.0 | 85.0 | 63.8 | 21.2 | 4.5 | 10.5 |
| 24.44 g Sodium Nitrate | 27.8 | 94.3 | 8.3 | 17.9 | 0.9 | 0.6 |
| 34.22 g Potassium Bromide | 27.0 | 98.4 | 15.6 | 11.0 | 0.3 | 0.2 |
| 23.58 g Sodium Acetate | 80.5 | 96.9 | 56.6 | 21.4 | 1.5 | 1.0 |
| 19.55 g Sodium Formate | 71.8 | 97.3 | 46.2 | 23.6 | 1.0 | 1.0 |
| 24.18 g Potassium Formate | 89.5 | 96.4 | 64.2 | 22.1 | 2.4 | 0.8 |
| 39.13 g $KH_2PO_4$ | 39.3 | 97.4 | 10.0 | 28.3 | 0.8 | 0.2 |

*Mole ratios are slightly higher: KOH/NB and TMACl/NB = 1.25

The results with KCl at a slightly lower mole ratio to nitrobenzene agree well with results obtained from the use of strong base and phase transfer catalyst (KOH and TMACl), with continuous distillation of the aniline-water azeotrope. This demonstrates that use of an inorganic salt and organic base is equivalent to use of a strong base and phase transfer catalyst. It may be noted that sodium is not as effective as potassium for completing the reaction. Nitrate and bromide are also less effective anions for reaction completion at the conditions of this example. However, it should be possible to increase conversion for these salts by modifying reaction conditions, such as increasing reaction temperature. Most significant is the positive effect of salt addition on reaction selectivity. Comparison of the second and third experiments in Table 1 above shows that with the addition of KCl only, azobenzene was reduced by nearly two-thirds and relatively small amounts of "Other" compounds such as 4-Phenazo-diphenylamine were formed. The "TMAH Only" run was also characterized by high levels of

TABLE 2

|  | Mole Ratio Salt/NB | Conversion % | Selectivity % | Yield, % | | | |
|---|---|---|---|---|---|---|---|
|  |  |  |  | p-NDPA | 4-NDPA | An Recr | Other |
| TMAH Only, No Salt Added | 0 | 100.0 | 83.8 | 62.4 | 21.4 | 4.4 | 11.8 |
| 4.66 g KCl | 0.25 | 100.0 | 87.1 | 63.4 | 23.7 | 7.8 | 5.1 |
| 13.05 g KCl | 0.70 | 100.0 | 93.8 | 72.3 | 21.5 | 5.0 | 1.2 |
| 21.44 g KCl | 1.15 | 100.0 | 97.2 | 72.3 | 24.8 | 1.5 | 1.4 |

Example 3

This example demonstrates the effect of adding a non-salt compound on selectivity and conversion of nitrobenzene. Reaction conditions were comparable to those for Example 1. Betaine, i.e. (acetyl)trimethylammomnium hydroxide inner salt, is a salt formed by the acetate group with the positively charged tetraalkylammonium group. So despite the name, the compound does not actually have hydroxide associated with the tetraalkylammonium group. However, when a strong base is added, betaine is converted to a compound that contains both an acetate salt group and a tetraalkylammonium hydroxide group. So with TMAH, betaine is converted to a compound with a tetramethylammonium-acetate group and an (acetyl) trimethylammomnium hydroxide group. With KOH, the compound has a potassium-acetate group with the (acetyl) trimethylammomnium hydroxide group. In the KOH case, the compound represents a metal organic salt and a organic base in one molecule. Betaine is known in the literature to be a phase transfer compound or PTC (Starks and Liotta, ibid), as it carries the inorganic or organic base into the organic phase.

The results in Table 3 show that betaine has only a modest effect on selectivity or conversion with TMAH. The results with betaine/NB=1.15 are only equivalent to KCl/NB=0.25. Furthermore, addition of an anion without an inorganic cation (ammonium acetate) is essentially ineffective. Therefore, the use of an inorganic salt or metal organic salt is the key to best results.

TABLE 3

| | Mole Ratio Mole Ratio to NB | Conversion % | Selectivity % | Yield, % | | | |
|---|---|---|---|---|---|---|---|
| | | | | p-NDPA | 4-NDPA | An Recr | Other |
| TMAH Only, No Salt or PTC Added | 0 | 100.0 | 83.8 | 62.4 | 21.4 | 4.4 | 11.8 |
| 4.66 g KCl | 0.25 | 100.0 | 87.1 | 63.4 | 23.7 | 7.8 | 5.1 |
| 21.44 g KCl | 1.15 | 100.0 | 97.2 | 72.3 | 24.8 | 1.5 | 1.4 |
| 22.16 g Ammonium Acetate | 1.15 | 0.5 | 100.0 | 0.3 | 0.2 | 0.0 | 0.0 |
| 33.68 g Betaine | 1.15 | 100.0 | 87.6 | 70.7 | 16.9 | 4.8 | 7.6 |

Example 4

This example illustrates that use of partial oxidative conditions can give a significant increase of selectivity. Reaction conditions were comparable to those for Example 1, except as indicated. The results are shown in Table 4. Reaction 1 had comparable conditions to those for Example 1 throughout. For Reaction 2, the air bleed was used only during nitrobenzene feed and was stopped when 75% of the feed was completed. For Reaction 3, the nitrobenzene feed time was shortened to 45 minutes and the hold time was increased to 60 minutes, while the air bleed was used only during the nitrobenzene feed time. It is expected that higher selectivity will also be attained or sulfate, carbonate and nitrate by use of partial oxidative conditions.

TABLE 4

| | Conversion % | Selectivity % | Yield, % | | | |
|---|---|---|---|---|---|---|
| | | | p-NDPA | 4-NDPA | An Recr | Other |
| 16.70 g KF-1 | 99.9 | 84.8 | 67.3 | 17.4 | 4.2 | 11.0 |
| 16.70 g KF-2 | 100.0 | 91.1 | 80.1 | 11.0 | 6.3 | 2.6 |
| 16.70 g KF-3 | 100.0 | 93.8 | 83.2 | 10.6 | 4.3 | 1.9 |

We claim:

1. A method of producing one or more 4-aminodiphenylamine intermediates comprising the steps of:
   (a) bringing an aniline or aniline derivative and nitrobenzene into reactive contact; and
   (b) reacting the aniline and nitrobenzene in a confined zone at a suitable time and temperature, in the presence of a mixture comprising an inorganic salt or metal organic salt, or mixtures thereof, having a cation that would be a suitable cation of a strong inorganic base, an oxidant and one or more of an organic base selected from the group of compounds defined by:

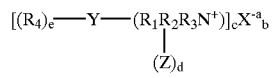

where $R_1$, $R_2$, $R_3$ are the same or different and selected from any straight chain or branched alkyl group containing from 1 to about 20 carbon atoms, e is a whole number integer of value 0, 1, 2 or 3, $(R_4)_e$ is hydrogen for e=0, $R_4$ is $R_1R_2R_3N^+$ for e=1, 2, or 3, X is an anion capable of abstracting a proton from the nitrogen of an aniline or aniline derivative, Y is alkyl, aryl, alkyl aryl or benzyl and substituted derivatives thereof, Z is a substituent selected from the group consisting of hydroxyl, halo, and other hetero atoms, where a=the valence of the anionic moiety and is a whole number integer of 1, 2, 3 or 4, b and c are whole number integers of value 1, 2, 3 or 4 and d is a whole number integer of value 0, 1, 2, 3 or 4, said mixture not including a reaction product of betaine and a strong inorganic base.

2. The method of claim 1 wherein said organic base is a quaternaryammonium hydroxide selected from the group consisting of tetramethylammonium hydroxide, tetrabutylammonium hydroxide, methyltributylammonium hydroxide, benzyltrimethylammonium hydroxide, tricaprylmethylammonium hydroxide, cetyltrimethylammonium hydroxide and choline hydroxide and equivalent quaternaryammonium alkoxides, acetates, carbonates, bicarbonates, cyanides, phenolics, phosphates, hydrogen phosphates, hypochlorites, borates, hydrogen borates, dihydrogen borates, sulfides, silicates, hydrogen silicates, dihydrogen silicates and trihydrogen silicates.

3. The method of claim 1 wherein the molar ratio of organic base to nitrobenzene is greater than or equal to about 1:1.

4. The method of claim 1 wherein the molar ratio of organic base to nitrobenzene is from about 1.1:1 to about 6:1.

5. The method of claim 1 wherein the mole ratio of inorganic salt or metal organic salt to nitrobenzene is from about 0.05:1 to about 6.5:1.

6. The method of claim 1 wherein the mole ratio of inorganic salt or metal organic salt to organic base is greater than or equal to about 1:1.

7. The method of claim 1 wherein said aniline derivative is selected from the group consisting of formanilide, phenylurea, carbanilide and thiocarbanilide.

8. The method of claim 1 wherein said aniline is a substituted aniline selected from the group consisting of 2-methoxyaniline, 4-methoxyaniline, 4-chloroaniline, p-toluidine, 4-nitroaniline, 3-bromoaniline, 3-bromo-4-aminotoluene, p-aminobenzoic acid, 2,4-diaminotoluene, 2,5-dichloroaniline, 1,4-phenylene diamine, 4,4'-methylene dianiline, 1,3,5-triaminobenzene, and mixtures thereof.

9. The method of claim 1 wherein substituted nitrobenzenes that may be used in accordance with the process of the present invention include o- and m-methylnitrobenzene, o- and m-ethylnitrobenzene, o- and m-methoxynitrobenzene, and mixtures thereof.

10. The method of claim 1 wherein said inorganic salt or metal organic salt used in conjunction with an organic base is selected from the group consisting of the fluoride, chloride, bromide, sulfate, hydrogen sulfate, nitrate, phosphate, formate, acetate and carbonate salts of cesium, rubidium, potassium and sodium and mixtures thereof.

11. The method of claim 1 wherein said oxidant is free oxygen.

12. The method of claim 1 wherein said oxidant is an oxidizing agent.

13. The method of claim 12 wherein said oxidizing agent is a peroxide.

14. The method of claim 12 wherein said oxidizing agent is hydrogen peroxide.

15. The method of claim 12 wherein said oxidizing agent is nitrobenzene.

16. The method of claim 1 wherein said oxidant is present only for part of the time during which the aniline and nitrobenzene react.

17. The method of claim 1 wherein said reactive contact is carried out at a temperature of from about 20° C. to about 150° C., a pressure in the range of from about 20 mbar to about 20 barg and a reaction time less than about 3.5 hours.

18. The method of claim 1 wherein the reaction of step (b) is carried out in the presence of not greater than about 10:1 moles water to moles nitrobenzene excluding water of hydration.

19. The method of claim 1 wherein said mixture comprising an organic base and an inorganic salt or metal organic salt is in aqueous solution and the reaction is carried out with a continuous distillation of aniline-water azeotrope.

20. The method of claim 1 wherein said reactive contact occurs in a suitable solvent system.

21. The method of claim 19 wherein said suitable solvent system comprises a polar aprotic solvent.

22. The method of claim 20 wherein said polar aprotic solvent is selected form the group consisting of dimethyl sulfoxide, benzyl ether, 1-Methyl-2-pyrrolidinone and N,N-dimethylformamide.

23. The method of claim 1 wherein said intermediates are hydrogenated to produce 4-aminodiphenylamine.

24. The method of claim 1 wherein X of formula I is selected from the group of anions consisting of hydroxide, alkoxide, acetate, carbonate, bicarbonate, cyanide, phenolic, phosphate, hydrogen phosphate, hypochlorite, borate, hydrogen borate, dihydrogen borate, sulfide, silicate, hydrogen silicate, dihydrogen silicate and trihydrogen silicate.

25. The method of claim 1 wherein said organic base is tetramethylammonium hydroxide, said inorganic salt includes a halide anion and the reaction is carried in aqueous solution with a continuous distillation of aniline-water azeotrope.

26. The method of claim 25 wherein said halide anion is chloride.

27. A method of producing one or more 4-aminodiphenylamine intermediates comprising the steps of:

bringing an aniline or aniline derivative and nitrobenzene into reactive contact; and reacting the aniline and nitrobenzene in a confined zone at a suitable time and temperature in the presence of a mixture comprising tetramethylammonium bromide, one or more inorganic bases and an oxidant, the reaction being carried in aqueous solution with a continuous distillation of aniline-water azeotrope.

* * * * *